(12) United States Patent
De Franciscis et al.

(10) Patent No.: US 8,741,870 B2
(45) Date of Patent: Jun. 3, 2014

(54) AXL RECEPTOR TYROSINE KINASE APTAMER INHIBITOR FOR USE IN THERAPY

(75) Inventors: Vittorio De Franciscis, Naples (IT); Laura Cerchia, Naples (IT)

(73) Assignee: Consiglio Nazionale delle Ricerche, Roma (IT)

( * ) Notice: Subject to any disclaimer, the term of this patent is extended or adjusted under 35 U.S.C. 154(b) by 0 days.

(21) Appl. No.: 13/876,103

(22) PCT Filed: Oct. 10, 2011

(86) PCT No.: PCT/EP2011/067624
§ 371 (c)(1),
(2), (4) Date: Mar. 26, 2013

(87) PCT Pub. No.: WO2012/049108
PCT Pub. Date: Apr. 19, 2012

(65) Prior Publication Data
US 2013/0197070 A1     Aug. 1, 2013

(30) Foreign Application Priority Data
Oct. 12, 2010   (IT) .............................. RM2010A0537

(51) Int. Cl.
*A61K 48/00*   (2006.01)
(52) U.S. Cl.
USPC ...................................................... 514/44 R
(58) Field of Classification Search
USPC ............................................. 514/44 A, 44 R
See application file for complete search history.

(56) References Cited

U.S. PATENT DOCUMENTS

2008/0227735 A1     9/2008   Tavitian et al.

FOREIGN PATENT DOCUMENTS

EP        2159286 A1     3/2010

OTHER PUBLICATIONS

Li, Y., et al: "Axl as a potential therapeutic target in cancer: role of Axl in tumor growth, metastasis and angiogenesis", Oncogene. Nature Publishing Group, GB, vol. 28. No. 39, Oct. 1, 2009, pp. 3442-3455, XP002601155, ISSN: 0950-9232, cited in the application: p. 3443, col. 1; p. 3451, col. 2-p. 3452, col. 1; p. 3453, col. 2; paragraph 2.
Ellington, A. D., et al: "In-vitro selection of RNA molecules that bind specific ligands", Nature, Nature Publishing Group, London, GB, vol. 346, No. 6287, Jan. 1, 1990, pp. 818-822, XP002547962, ISSN: 0028-0836, DOI: DOI:10.1038/346818AO, cited in the application p. 818-p. 821.

*Primary Examiner* — Jon E Angell
(74) *Attorney, Agent, or Firm* — Lucas & Mercanti, LLP

(57) ABSTRACT

The present invention concerns a nucleotide aptamer having the sequence: 5'-AUGAUCAAUCGCCUCAAUUCGA-CAGGAGGCUCAC-3'(SEQ ID NO: 1) for use in the treatment and/or prevention and/or diagnosis of an Axl receptor tyrosine kinase induced disorder and a pharmaceutical composition comprising the same. The invention also relates to a method for the diagnosis of an Axl receptor tyrosine kinase induced disorder in a patient from which a sample is obtained and related diagnostic kit.

6 Claims, 8 Drawing Sheets

A

GL21 52-85 : AUGAUCAAUCGCCUCAAUUCGACAGGAGGCUCAC

B

A

B

A

B

SEQUENCE LISTING

<160> NUMBER OF SEQ ID NOS: 3

<210> SEQ ID NO 1
<211> LENGTH: 34
<212> TYPE: RNA

```
<213> ORGANISM: Artificial Sequence
<220> FEATURE:
<223> OTHER INFORMATION: synthetic aptamer

<400> SEQUENCE: 1
augaucaauc gccucaauuc gacaggaggc ucac                          34

<210> SEQ ID NO 2
<211> LENGTH: 39
<212> TYPE: RNA
<213> ORGANISM: Artificial Sequence
<220> FEATURE:
<223> OTHER INFORMATION: synthetic control aptamer

<400> SEQUENCE: 2
uucguaccgg guagguuggc uugcacauag aacguguca                     39

<210> SEQ ID NO 3
<211> LENGTH: 97
<212> TYPE: DNA
<213> ORGANISM: Artificial Sequence
<220> FEATURE:
<223> OTHER INFORMATION: synthetic hairpin

<400> SEQUENCE: 3
tgctgttgac agtgagcgcg ctccaagatt ctagatgatt tagtgaagcc acagatgtaa    60
atcatctaga atcttggagc atgcctactg cctcgga                            97
```

AXL RECEPTOR TYROSINE KINASE APTAMER INHIBITOR FOR USE IN THERAPY

CROSS-REFERENCE TO RELATED APPLICATIONS

This application is a 371 of PCT/EP2011/067624, filed Oct. 10, 2011, which claims the benefit of Italian Patent Application No. RM2010A000537, filed Oct. 12, 2010, the contents of each of which are incorporated herein by reference.

FIELD OF THE INVENTION

The invention relates to the identification of a nucleotide aptamer and its target, the Axl receptor tyrosine kinase. The aptamer acts as an inhibitor of the Axl receptor tyrosine kinase and is thus suitable for use in the treatment and/or the diagnosis of a AXL receptor tyrosine kinase induced disorder.

BACKGROUND TO THE INVENTION

The rapid expansion of new technologies for molecular diagnostics and tumor-targeted therapy has increased the need to develop highly specific targeting ligands for cell surface molecules that are expressed differentially in tumor cells or tissues.

Axl is a member of a receptor tyrosine kinases (RTK) family that also includes Dtk and Mer (Hafizi and Dahlbäck, 2006) and is activated by the growth factor, growth arrest specific 6 (GAS6). Ligand-induced stimulation of Axl mediates the activation of multiple downstream signaling pathways which play pivotal roles in regulating growth, proliferation and survival.

Axl was originally identified as a transforming gene in patients with chronic myelogenous leukemia (O'Bryan et al., 1991; Janssen et al., 1991). Subsequently Gash-Axl signaling has been implicated in a host of discrete cellular responses including cell survival, proliferation, migration, and adhesion (Linger et al., 2008). Overexpression of Axl has been associated with invasiveness and metastasis in a wide array of human cancers including lung (Shieh et al., 2005), prostate (Sainaghi et al., 2005), breast (Meric et al., 2002; Zhang et al., 2008), gastric (Wu et al., 2002) and pancreatic (Koorstra et al., 2009) cancers, renal cell carcinoma (Chung et al., 2003) as well as glioblastoma (Vajkoczy P, et al., 2006; Hutterer et al., 2008).

These data indicate that Axl signaling represents a novel target class for tumor therapeutic development.

An emerging wave of targeted therapeutic molecules against RTKs is composed of nucleic acid-based aptamers. They are short, structured single-stranded RNA or DNA ligands that bind with high affinity to their target molecules. Aptamers are isolated by the Systematic Evolution of Ligands by EXponential enrichment (SELEX) technology that since its first description in 1990 (Ellington and Szostak, 1990; Tuek and Gold, 1990), has yielded several high-affinity ligands of a wide variety of targets ranging from small chemical compounds to cells and tissues (Cerchia et al., 2002; Cerchia and de Franciscis, 2010). Aptamers are now emerging as promising molecules to target specific cancer epitopes in clinical diagnosis and therapy. Because of their high specificity and low toxicity, aptamers might be considered as the compounds of choice for in vivo cell recognition. In this perspective, nucleic acid aptamers represent a class of ligands that can rival antibodies for specificity and affinity for the target and is coupled to slow degradation kinetics and low toxicity. Furthermore, aptamers can be readily chemically modified by the addition of polyethylene glycol and other moieties to enhance their bioavailability and pharmacokinetics.

To date, only few inhibitors of Axl have been reported that are completely unrelated to the anti-Axl aptamer both from the structural and mode of action point of view:

1) small-molecule inhibitors, such as R428, that block the catalytic activities of Axl (Holland et al., 2010; Zhang et al., 2008);

2) an anti-Axl monoclonal antibody that blocks the ligand Gas6 binding to the receptor (Ye et al., 2010) proteins derived from the extracellular domain of Axl that inhibit its action by competing for ligand (GAS6) binding (International Patent application WO2008098139).

The present invention has identified an aptamer, GL21 52-85, that can solve the major problems related to the in vivo use of prior art inhibitors. GL21 52-85 aptamer is highly specific for the Axl receptor whereas R428 is effective not only on Axl but also on other tyrosine and serine/threonine kinases (i.e. Tie-2, Flt-1, Flt-3, Ret, Abl). Compared to anti-Axl antibodies, both antibodies and the anti-Axl aptamer have binding affinities in the low nanomolar range. However, the aptamer lacks immunogenicity, whereas antibodies in humans are significantly immunogenic, thus precluding repeat dosing unless they are "humanized" or produced fully human. RNA-based therapeutics are thus likely to be safer when repeated administrations are necessary. Further, the aptamer contains pyrimidines modified at the 2'-position, which render the RNA resistant to extracellular nucleases and even less immunogenic than natural RNA. Moreover, the aptamer can be readily chemically modified by the chemical addition of poly(ethylene glycol) (PEG) and other moieties to enhance bioavailability and pharmacokinetic properties. Because aptamers are synthesized by solid phase chemical synthesis, conjugation chemistry is possible at any position in the molecule at difference of proteins and peptides that can accept conjugation only on specific residues.

Further, GL21 52-85 offers several advantages over monoclonal antibodies due to its specificity and affinity for the target, slow degradation kinetics and low toxicity.

BRIEF DESCRIPTION OF THE INVENTION

In the present invention, the authors have identified a synthetic nuclease resistant RNA aptamer 34 nucleotide-long, named GL21 52-85, that binds to Axl receptor at high affinity causing inhibition of cell proliferation in vitro and in vivo.

The authors' results indicate that this neutralizing RNA-aptamer represents an innovative tool to develop cancer therapeutic and diagnostic strategies specifically targeting the Axl receptor.

It is therefore an object of the invention a nucleotide aptamer having the sequence: 5'-AUGAUCAAUCGCCU-CAAUUCGACAGGAGGCUCAC-3'(SEQ ID NO: 1) for use in the treatment and/or prevention and/or diagnosis of an Axl receptor tyrosine kinase induced disorder.

Preferably the nucleotide aptamer is nuclease-resistant. Still preferably the nucleotide aptamer has at least one or all of the pyrimidine residues that are modified to 2'-fluoropyrimidines. In the present invention, the pyrimidine residues may also be modified as 2'-O-alkyl nucleotides, or 3' end cap and locked nucleic acids or as LNA modifications to significantly enhance RNA stability.

Preferably the Axl receptor tyrosine kinase induced disorder is caused by, associated with and/or accompanied by Axl kinase hyperfunction.

Still preferably the Axl receptor tyrosine kinase induced disorder is selected among hyperproliferative disorders.

In a preferred embodiment, the Axl receptor tyrosine kinase induced hyperproliferative disorder is selected from the group consisting of cancer or primary tumour metastasis.

Yet preferably the cancer or primary tumour metastasis is selected from the group of: breast cancer, colon cancer, prostate cancer, lung cancer, gastric cancer, ovarian cancer, endometrial cancer, renal cancer, hepatocellular cancer, thyroid cancer, uterine cancer, esophageal carcinoma, squamous cell carcinoma, leukemia, osteosarcoma, melanoma, glioblastoma, neuroblastoma, or primary tumour metastasis.

It is a further object of the invention a pharmaceutical composition comprising the nucleotide aptamer as defined above for use in the treatment and/or prevention of an Axl receptor tyrosine kinase induced disorder.

Preferably the pharmaceutical composition further comprises another therapeutic agent. It is a further object of the invention a method for the diagnosis of an Axl receptor tyrosine kinase induced disorder in a patient from which a sample is obtained comprising:
  incubating the sample with the nucleotide aptamer as defined above;
  measuring the binding of the nucleotide aptamer to the sample.

Preferably the sample is a blood, serum or saliva sample, a biopsy, urine or cerebrospinal fluid.

It is a further object of the invention a kit for the diagnosis of an Axl receptor tyrosine kinase induced disorder in a patient from which a sample is obtained comprising the nucleotide aptamer of the present invention.

The invention will be now illustrated by means of non limiting examples referring to the following figures.

BRIEF DESCRIPTION OF THE SEQUENCE LISTING

Figure 1:
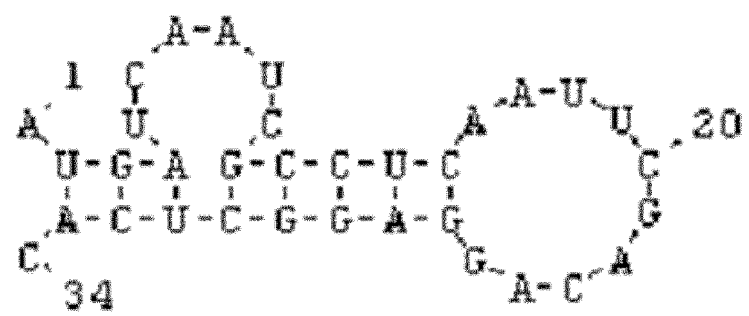
FIG. 1. GL21 52-85 aptamer. A) Nucleotidic sequence of GL21 52-85 aptamer. All the pyrimidines of the sequence are 2'-fluoropyrimidine (2'F-Py), labelled in underlined. B) Secondary structure predicted for GL21 52-85 aptamer by using MFOLD software version 3.1 (available at http://www.bioinfo.rpi.edu/applications/mfold/).
Figure 2:
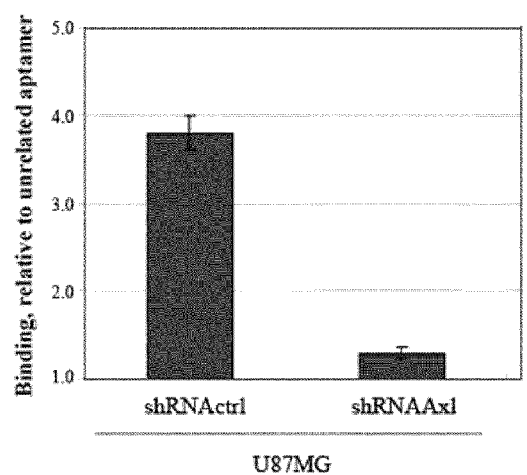
FIG. 2. Binding of GL21 52-85 aptamer following Axl gene silencing/expression. A) Binding of GL21 52-85 aptamer on glioma U87MG cells transfected with a specific Axl shRNA (shRNA Axl) or with a non-related shRNA (shRNActrl) that does not target Axl as a control. A1) cell lysates from U87MG cells transfected with a specific Axl shRNA or control shRNA were immunoblotted with anti-Axl (Axl) antibodies. Filters were stripped and reprobed with anti-αtubulin antibodies to confirm equal loading. Values below the blots indicate signal levels relative to control arbitrarily set to 1 (labeled with asterisk). Intensity of bands has been calculated using the NIH Image Program on at least two different expositions to assure the linearity of each acquisition. B) binding of GL21 52-85 aptamer on breast SKBr3 transfected (or not) with Axl. B1) cell lysates from U87MG cells or SKBr3 transfected (or not) with Axl were immunoblotted with Axl antibodies. To confirm equal loading, filters were reprobed with anti-αtubulin antibodies. In A and B) Binding was performed incubating [$^{32}$P]-labeled aptamer on the cells in the same condition at 50 nM. The results are expressed relative to the background binding detected with a non-functional unrelated aptamer used as a negative control.
Figure 2:
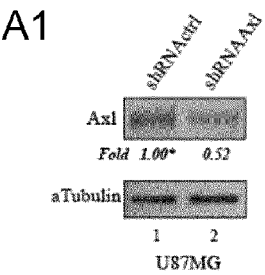
Figure 2:
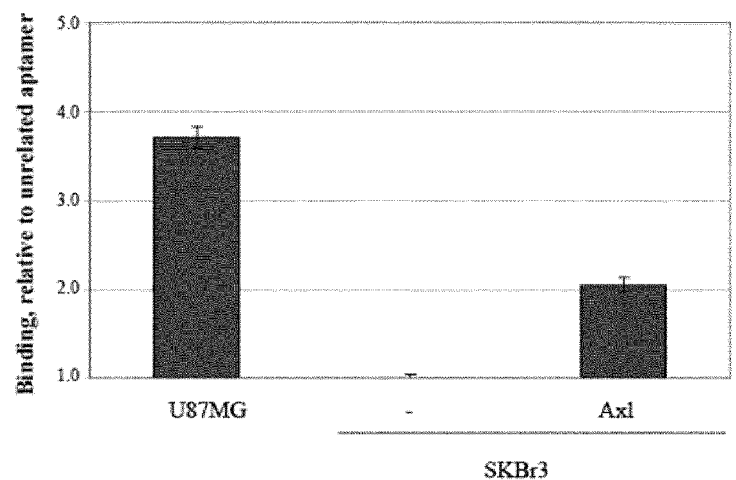
Figure 2:
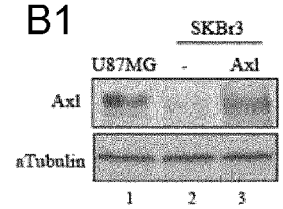

SEQ ID NO: 1 sets out sequence from the 5' of the aptamer, GL21 52-85 (see also FIG. 1), 5' AUGAUCAAUCGCCUCAAUUCGACAGGAGGCUCAC 3'.

SEQ ID NO: 2 sets out sequence from the 5' of the non-functional unrelated aptamer used as negative control in FIG. 2, FIG. 3, FIG. 4-6: 5' UUCGUACCGGGUAGGUUGGCU-UGCACAUAGAACGUGUCA 3'

SEQ ID NO: 3 sets out the sequence of a high performance short hairpin RNA (shRNA) specifically targeting Axl (oligo ID V2HS_201787) TGCTGTTGACAGTGAGCGCGCTC-CAAGATTCTAGATGATTTAGTGAAGCCACA GATG-TAAATCATCTAGAATCTTGGAGCATGC-CTACTGCCTCGGA

DETAILED DESCRIPTION OF THE INVENTION

Materials and Methods

GL21 52-85 Aptamer

GL21 52-85 is a 2'-fluoropyrimidine (2'F-Py) nuclease-resistant RNA aptamer consisting of 34 nt: 5'AUGAUCAAUCGCCUCAAUUCGACAGGAG-GCUCAC3' (SEQ ID NO: 1) GL21 52-85 and an unrelated sequence used as a negative control were purchased from Sigma (Sigma, St. Louis, Mo.).

Cell Lines and Transfection

Human glioma U87MG, human breast SKBr3, MCF7, MDA-MB-231 cells and epidermoid carcinoma A431 (all from American Type Culture Collection, Manassas, Va.), were grown in Dulbecco's modified Eagle medium (DMEM) supplemented with 10% fetal bovine serum (FBS) and 2 mM L-glutamine (Invitrogen, Carlsbad, Calif.).

Axl gene silencing in glioma U87MG cells was established by transfection of an high performance short hairpin RNA (shRNA) specifically targeting Axl (from Expression Arrest™ Human shRNA Collection, Open Biosystems, Huntsville, Ala.). Controls were performed using a non-related shRNA (shRNActrl) that do not lead to the specific degradation of Axl mRNA Open Biosystem (cat. Number RHS1707). Axl expression in human breast SKBr3 cells was obtained by transfection of Axl TruClone (Origene, Rockville, Md.).

Cells ($3.5 \times 10^5$ cells per 6 cm plate) were grown and overlaid with the transfection mixtures containing the shRNA against Axl or Axl TruClone (6 μg) and Lipofectamine 2000 (Invitrogen, Carlsbad, Calif.) in Opti-MEM I reduced serum medium (Invitrogen). After 5 hours incubation, complete culture medium was added to the cells and incubation was prolonged up to 72 hs. For binding assays transfected cells were plated in 24 well plates after 24 hs from transfection.

Binding Assays

Binding experiments were performed with 5'-[$^{32}$P]-labeled RNA. For labeling 2'-F-Py RNAs were 5'-end dephosphorylated using bacterial alcaline phosphatase (Invitrogen, Carlsbad, Calif.) before [$^{32}$P]-5'-end-labeled using T4 kinase (Invitrogen) and γ-[$^{32}$P]-ATP ($6 \times 10^3$ Ci/mmol, GE Healthcare Bio-Sciences, Uppsala, Sweden) according to the supplier's instructions.

For binding on cells, $3.5 \times 10^4$ cells were plated in 24-well plates in triplicate and were incubated with GL21 52-85 aptamer or unrelated sequence used as a negative control at 50 nM concentration in 200 μl of DMEM serum free for 20 min at RT in the presence of 100 μg/ml polyinosine as a nonspecific competitor (Sigma, St. Louis, Mo.). After five washings with 500 μl DMEM, bound sequences were recovered in 300 μl of SDS 1%, and the amount of radioactivity recovered was counted.

The aptamers ability to bind Axl, Dtk and Mer soluble extracellular domain was investigated by filter binding by plotting the fraction of RNA bound to the nitrocellulose filter as a function of protein concentration, using the following equation:

$$RNA\ bound = \frac{B\max[\text{Protein}]}{Kd + [\text{Protein}]}$$

Where Bmax is the extrapolated maximal amount of RNA protein complex that will be bound.

1 nM of radiolabelled aptamers (GL21 52-85 or Unrelated) were incubated with 1, 3.2, 10, 32, 100, 320 and 1000 nM of Axl, Dtk, Mer soluble extracellular domain (all from R&D Systems, Minneapolis, Minn.) for 15 min at 37° in phosphate-buffered saline (PBS) supplemented with 0.01% bovine serum albumin.

After incubation, the aptamer-protein mix was passed through nitrocellulose membrane filter (Millipore Co., Bedford, Mass.) and filters were counted.

In all binding assays the background values obtained with the unrelated RNA aptamer were subtracted from the values obtained with the GL21 52-85 specific aptamer.

Immunoblot Analyses

To assess the effects of aptamers on Axl activity, U87MG cells ($1.5 \times 10^5$ cells per 3.5-cm plate) were serum-starved overnight, pretreated with 200 nM GL21 52-85 aptamer or the unrelated aptamer used as a negative control for 3 h and then stimulated for 30 min with 400 ng/ml Gas6 (R&D Systems, Minneapolis, Minn.) either alone or in presence of each aptamer. The aptamers were subjected to a short denaturation-renaturation step (85° C. for 5 min, snap-cooled on ice for 2 min, and allowed to warm up to 37° C.) before each treatments.

To prepare cell extracts, cells were washed twice in ice-cold PBS, and lysed in buffer A (50 mMTris-HCl pH 8.0 buffer containing 150 mMNaCl, 1% Nonidet P-40, 2 mg/ml aprotinin, 1 mg/ml pepstatin, 2 mg/ml leupeptin, 1 mM Na$_3$VO$_4$). Protein concentration was determined by the Bradford assay using bovine serum albumin as the standard. The cell lysates were subjected to SDS-PAGE. Gels were electroblotted into polyvinylidene difluoride membranes (Millipore Co., Bedford, Mass.), and filters were probed with the indicated primary antibodies: anti-Axl and anti-phospho-Axl (R&D Systems); anti-ERK1 (C-16) (Santa Cruz Biotechnology, Calif., USA); anti-phospho-44/42 MAP kinase (E10) (also indicated as p-Erk) (Cell Signaling, Beverly, Mass.); anti-α-αtubulin (DM 1A) (Sigma, St. Louis, Mo.).

Proteins were visualized with peroxidase-conjugated secondary antibodies using the enhanced chemiluminescence system (GE Healthcare Bio-Sciences, Uppsala, Sweden). Where indicated, filters were stripped in 62.5 mM Tris-HCl pH 6.8 with 100 mM 2-mercaptoethanol and 2% SDS for 30 min at 54° C., and reprobed.

Cell Viability Assay

Cell viability was assessed with CellTiter 96® AQueous One Solution Cell Proliferation Assay (Promega, Madison, Wis.) according to according to the supplier's instructions. Cells ($4 \times 10^3$ cells/well) were plated in 96-well plates in triplicate and were treated for 24 hs with heat denatured GL21 52-85 or the unrelated aptamer at 3 μM concentration. RNA concentrations were determined to ensure the continuous presence of a concentration of at least 200 nM, which takes into account the 6 hs-half life of the aptamer in 10% serum. The optical density (OD) was measured using a Multilabel Counter (Bio-Rad) at a wavelength of 490 nm and cell viability was calculated by the following formula:

Cell viability(%)=(OD treated cells/OD control cells)×100%.

Transwell Migration Assay

A549 or U87 MG cells were pre-treated with 200 nMGL21 52-85 aptamer or unrelated aptamer and following 3 h trypsinized, re-suspended in DMEM serum free, and counted. Cells ($10 \times 10^4$ in 100 µl serum-free medium per well) were then plated into the upper chamber of a 24-well transwell (Corning). Cells were exposed in the presence of Gas6 (400 ng/ml) as an inducer of migration in serum-free medium (0.6 ml) in the lower chamber, or were exposed in the presence of 10% FBS. After incubation at 37° C. in humidified 5% CO2 for 24 hs, cells were visualized by Crystal violet staining.

Soft-Agar Colony Formation Assay $10^4$ U87MG or A549 cells were plated in 60 mm dishes in a solution containing Dulbecco's modified Eagle's medium 2× (Sigma, St Louis, Mo., USA), Tryptose Phosphate Broth (Difco, B D, Franklin Lakes, N.J., USA), and 1.25% of Noble Agar (Difco). Briefly, cells were harvested and counted then a layer of 7 ml with the solution containing Noble Agar were left to polymerize on the bottom of the dishes. Then cells were re-suspended in 2 ml of same solution and plated. Cells were left grown for 2 weeks in the incubator.

Spheroid Formation Assay

Cells were grown in DMEM-F12 supplemented with 1% B-27, human recombinant bFGF (10 ng/mL), and EGF (20 ng/mL). The number of spheroid-forming colonies was counted after 10 days.

In Vivo Experiments

Athymic nude mice (nu/nu) were maintained in a sterile environment according to guidelines established by the US Department of Agriculture and the American Association for Accreditation of Laboratory Animal Care (AAALAC).

Mice were inoculated with either $3 \times 10^6$ (in 100 µl) in vitro propagated MDA-MB-231 or A549 cells subcutaneously injected into each flank. Approximately 24 non-necrotic tumors for each tumor type, of about 1 cm in diameter, were randomly divided into three groups of eight mice per treatment group as follows: group 1, no treatment; group 2, treated with unrelated RNA as a negative control (200 pmols/injection); group 3, treated with GL21 52-85 (200 pmols/injection). Compounds were injected intra-tumorally in 100-µl volumes three times a week for two weeks. Day 0 marks the first day of injection. Aptamers may also be administrated systemically, in particular when optimized by addition of polyethyleneglycol (PEG).

The volume injections are small enough to preclude the compounds being forced inside the cells due to a nonspecific high-pressure injection. Tumors were measured every 3 days with calipers in three dimensions. The following formula was used to calculate tumor volume: $V_T = (W \times L \times H) \times 0.5236$ (W, the shortest dimension; L, the longest dimension, H, intermediate dimension). The growth curves are plotted as the means tumor volume±s.e.m. Statistical analysis of tumor size data was conducted using a one-way ANOVA. A P-value of 0.05 or less was considered to indicate a statistically significant difference.

Results

GL21 52-85 is a RNA-Aptamer Interacting with the Axl RTK

GL21 52-85 is a 2'-fluoropyrimidine (2'F-Py), nuclease-resistant RNA aptamer consisting of 34 nt (FIG. 1). It was obtained by reducing the length of the aptamer GL21 (92 mer) that the authors have previously generated by a differential cell-SELEX approach on tumorigenic glioblastoma U87MG cells. The adopted selection strategy has been published and is disclosed in the International Patent Application WO 2010/023327.

The GL21 52-85 aptamer binds to U87MG target cells with a Kd of 90 nM.

The authors have identified the Axl receptor as the target of GL21 52-85 aptamer. Indeed, the ability of GL21 52-85 aptamer to bind to U87MG cells is significantly reduced upon decreased Axl expression by means of a specific shRNA (FIG. 2A). Conversely, GL21 52-85 aptamer binds breast SKBr3 cells transfected with human Axl while it shows no binding on parental SKBr3 cells that do not express Axl receptor (FIG. 2B).

Figure 3:
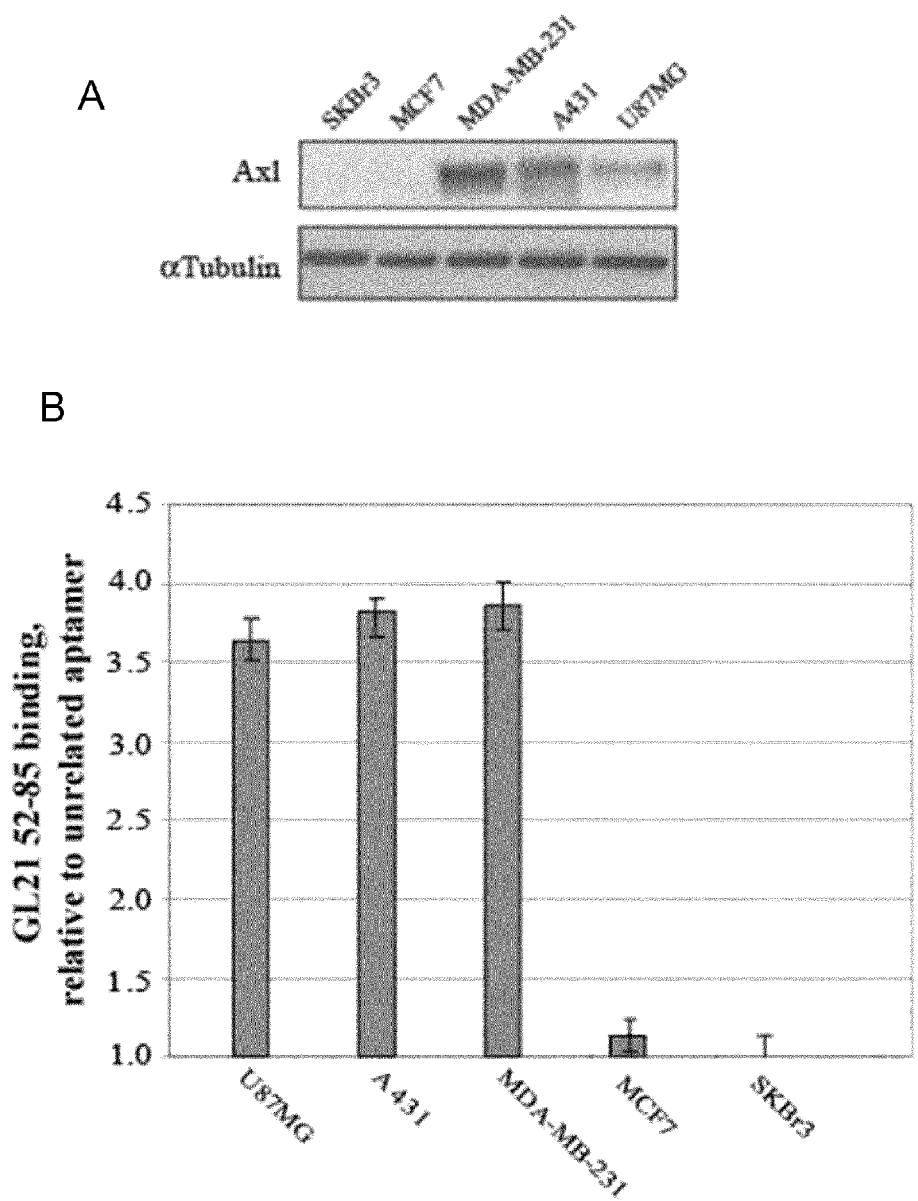
FIG. 3. Binding of GL21 52-85 aptamer on different cancer cells. A) Cell lysates from the indicated cell lines were immunoblotted with anti-Axl (Axl) antibodies. Filters were stripped and reprobed with anti-αtubulin antibodies to confirm equal loading. B) Binding of GL21 52-85 aptamer on the indicated cell lines, was performed incubating [$^{32}$P]-labeled aptamer on the cells in the same condition at 50 nM. The results are expressed relative to the background binding detected with the unrelated aptamer.

Accordingly, binding analyses with the GL21 52-85 aptamer on different cancer cell lines that display a different expression of Axl show a correlation between the binding of the aptamer and Axl expression (FIG. 3). Indeed, among the cells tested GL21 52-85 aptamer binds Axl-positive human glioma U87MG, breast MDA-MB-231 and epidermoid carcinoma A431 cells, whereas it does not bind to breast MCF7 and SKBr3 cells that do not express the receptor.

Figure 4:
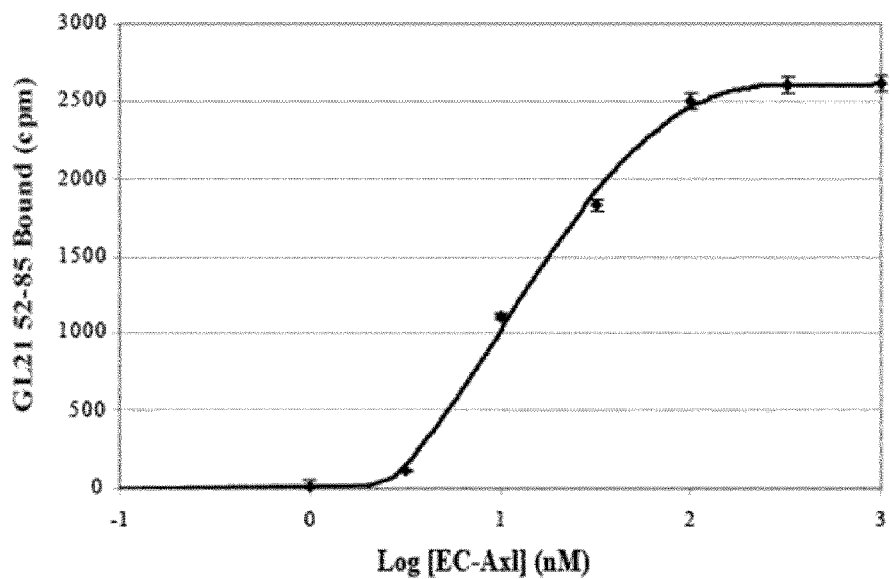
FIG. 4. Binding on purified Axl and Dtk receptors. GL21 52-85 aptamer was incubated with A) the soluble extracellular domain of Axl (EC-Axl) and B) the soluble extracellular domain of Dtk (EC-Dtk). Dissociation constants (Kd values) of the aptamer were calculated as reported in Materials and Methods.
Figure 4:
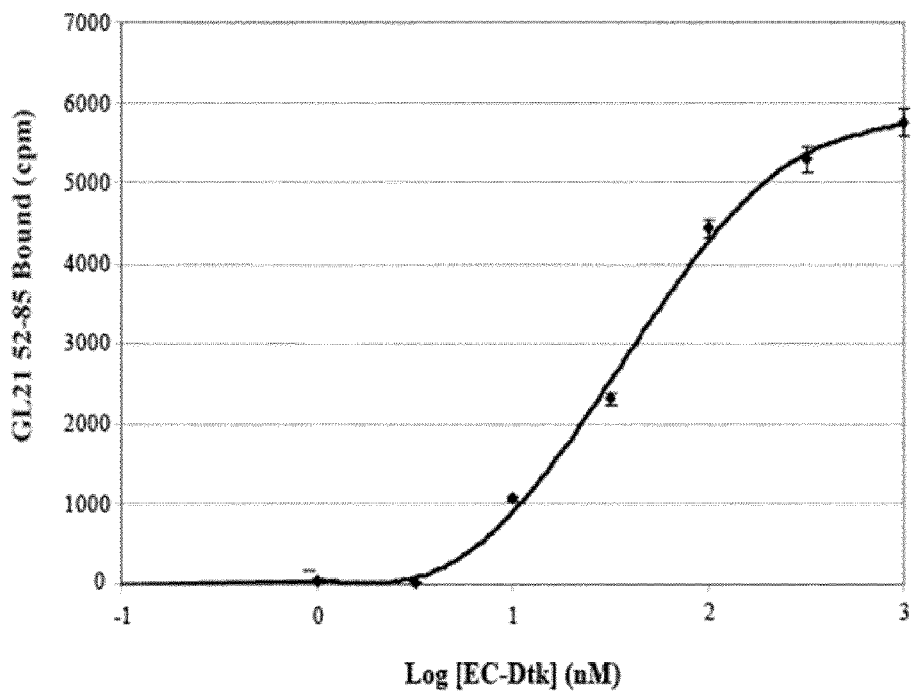
Figure 5:
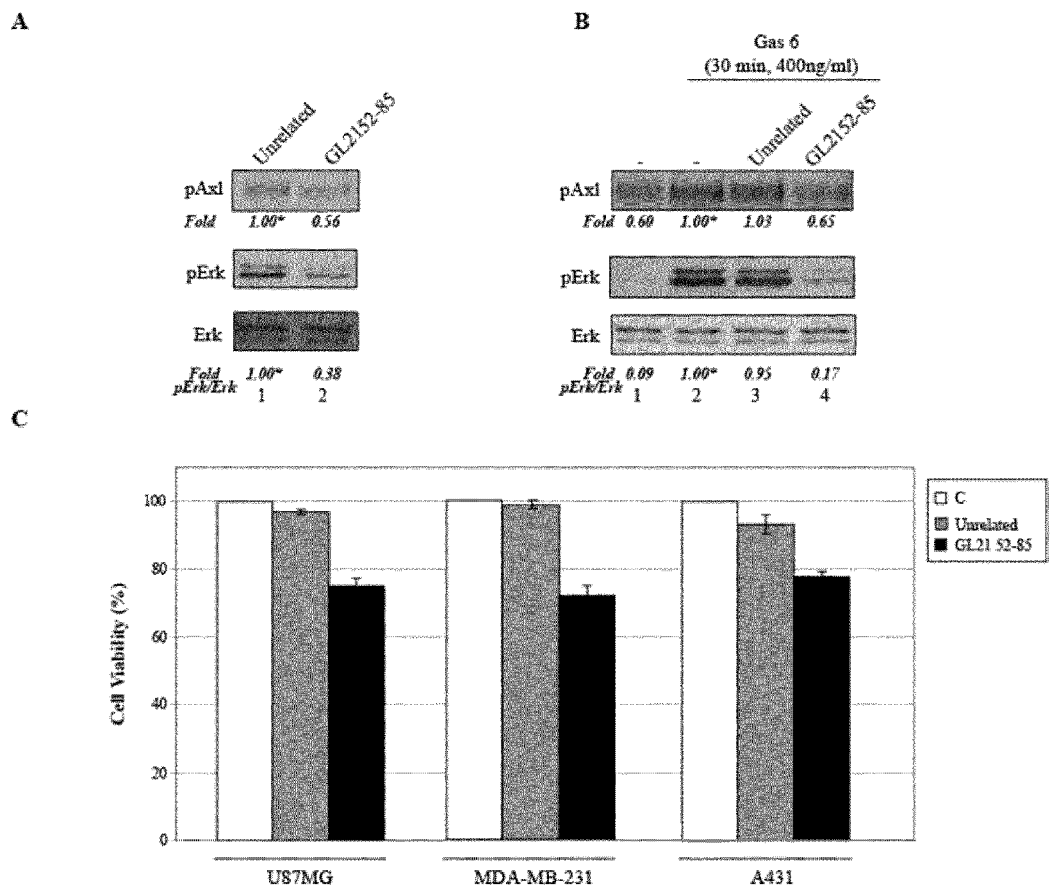
FIG. 5. GL21 52-85 aptamer inhibits Axl Activity. A) U87MG cells were treated with GL21 52-85 or unrelated aptamer for 3 h; B) serum starved U87MG were either left untreated or treated for 3 h with GL21 52-85 or the unrelated aptamer and then stimulated with Gas 6 ligand. In A and B, cell lysates were immunoblotted with anti-(phospho)-Axl (pAxl), anti-Axl (Axl) or anti-(phospho)-ERK (pErk), as indicated. Filters were stripped and reprobed with anti-ERK (Erk) or anti-αtubulin antibodies to confirm equal loading. Values below the blots indicate signal levels relative to Gas 6 stimulated controls arbitrarily set to 1 (labeled with asterisk). Intensity of bands have been calculated using the NIH Image Program on at least two different expositions to assure the linearity of each acquisition. C) Effect on cell viability. U87MG, A431 or MDA-MB-231 cells were left untreated (C) or treated for 24 hrs with GL21 52-85 or unrelated aptamer at 200 nM final concentration. Cell viability was analyzed as reported in Materials and Methods by MTT assay. The results are expressed relative to untreated cells arbitrary set to 100% of viability and are representative of at least three different experiments.
Figure 6:
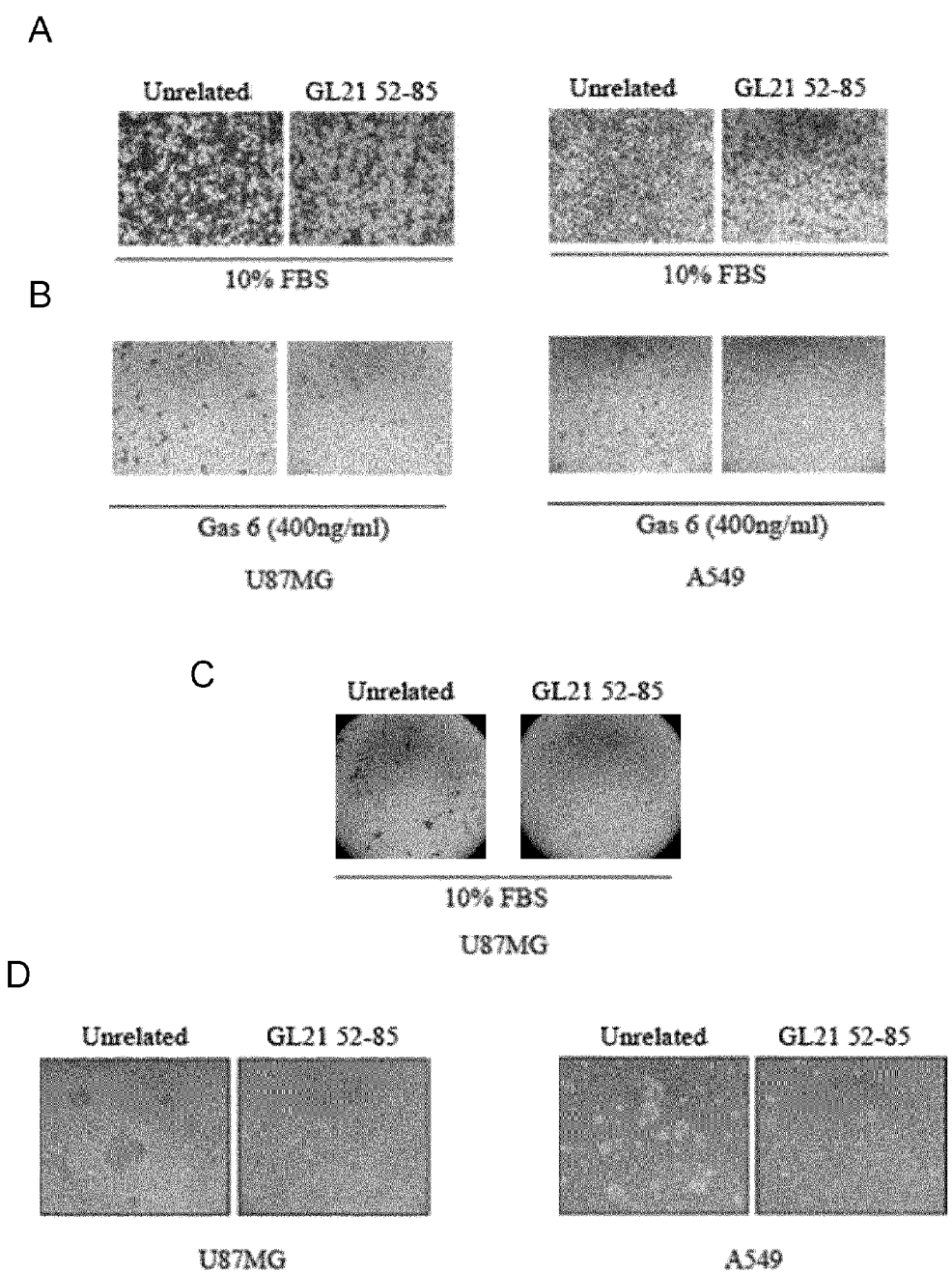
FIG. 6. GL21 52-85 aptamer inhibits cell migration and invasion. Motility of U87MG (Left panels) and A549 (Right panels) cells was analyzed by Transwell Migration Assay for 24 h toward 10% FBS (A) or serum free medium containing Gas6 (B) as a chemo-attractant. The cells that had migrated to the lower surface were stained with crystal violet and photographed. (C) U87MG invasion through Matrigel toward 10% FBS was carried out in the presence of GL21 52-85 aptamer or the unrelated aptamer for 24 h. (D) Soft Agar Colony formation assay in the presence of GL21 52-85 or the unrelated aptamer, using U87MG (left panel) or A549 (right panel).

The GL21 52-85 aptamer recognizes specifically the Axl receptor expressed on the surface of cancer cells as well as the purified soluble extracellular domain of the receptor (FIG. 4). Indeed, a filter binding analysis performed with the soluble extracellular domain of Axl (indicated as EC-Axl) confirmed a strong affinity of GL21 52-85 for EC-Axl (Kd of 13 nM) whereas a lower affinity (kd of 47 nM) was obtained for the extracellular domain of Dtk (indicated as EC-Dtk). Regarding the binding to the extracellular domain of Mer (EC-Mer), under the protein concentration used, no Kd value could be calculated indicating that the aptamer does not bind to EC-Mer or binds to the protein but with an affinity of a magnitude at least $10^3$ lower.

For comparison, R428 exhibits an EC50/IC50 of 14 nmol/L in in vitro biochemical kinase assays using recombinant Axl protein (Holland et al., 2010). The Kd value of Axl mAb YW327.6S2 vs human Axl is of about 1 nM (Ye et al, 2010). SKI-606 and NA80x1 inhibit AXL kinase activity with an IC50 of 0.56±0.08 micromol/L and 12.67±0.45 micromol/L, respectively (Zhang et al, 2008 and WO2009127417).

GL21 52-85 Inhibits Axl Activity

The identification of an aptamer that binds to Axl receptor raises the obvious question of whether this aptamer may interfere with the receptor activity.

Thus, the authors analysed whether GL21 52-85 could inhibit Axl phosphorylation both in basal condition (FIG. 5A) and following Gas6 stimulation of Axl-positive U87MG cells (FIG. 5B). As shown in FIG. 5A, the GL21 52-85 aptamer, at a concentration of 200 Nm, strongly inhibits phosphorylation of Axl and of the downstream effector ERK. Furthermore, it drastically reduced the Gas6-dependent phosphorylation of Axl and ERK (FIG. 5B).

Figure 7:
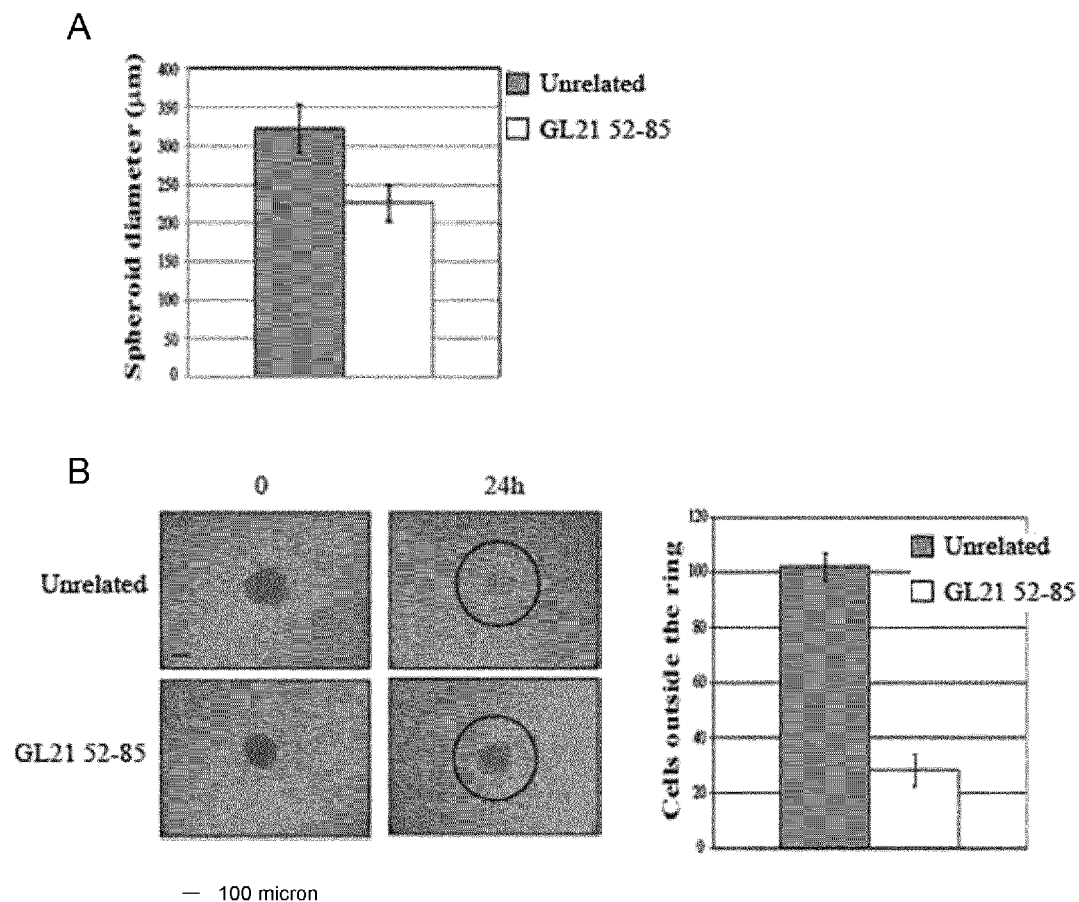
FIG. 7. GL21 52-85 aptamer inhibitsspheroid formation. (A) Spheroids diameter has been measured and the mean value following 10 days of GL21 52-85 or unrelated aptamer-treatment has been calculated. (B) Spheroids average approximately 200 μm in diameter were seeded onto 24-well plates and allowed to adhere and migrate overnight. Representative photographs of the spheroids before and after migration are shown (Left panels). Quantification of U87MG cells migrated from the initial spheroids, error bars depict means±s.d. (n=10) (Right panel).

As next step, the authors checked the effect of GL21 52-85 on cell growth of Axl-positive cells by MTT assay. U87MG, MDA-MB-231 or A431 cells were treated for 24 hrs with GL21 52-85 aptamer or unrelated RNA as negative control. GL21 52-85 aptamer reduces cell viability of all cell lines by comparison with untreated cells or treated with the control RNA (FIG. 5C). The authors further examined the effects of GL21 52-85 aptamer on U87MG (Left panels) and A549 (Right panels) cell migration, and found that cells treated with the GL21 52-85 aptamer have a decreased capacity in motility in comparison with the cells treated with the unrelated sequence in Transwell Migration Assay either in the presence of 10% FBS (FIG. 6A) or in the presence of Gas6 as chemoattractant (FIG. 6B). Accordingly, GL21 52-85 aptamer strongly reduces U87MG cell invasion in the presence of 10% FBS (FIG. 6C). Furthermore, GL21 52-85 reduces the number of colonies in Soft Agar Colony Formation Assay (FIG. 6D) in comparison with the unrelated sequence, either in U87MG (Left panels) or in A549 cells (Right panels). Then, the authors demonstrated that GL21 52-85 aptamer interferes with spheroid formation of U87MG cells (B), in comparison with the unrelated sequence, reducing the spheroid size (FIG. 7 A) and the migration of treated U87MG-treated cells from the initial spheroids (FIG. 7 B).

GL21 52-85 Suppresses Tumor Growth In Vivo

It has been reported that inhibition of Axl significantly attenuated tumor growth (Li et al., 2009; Ye et al., 2010; Holland et al., 2010). Thus, the authors evaluated GL21 52-85 aptamer on xenograft tumor growth.

Figure 8:
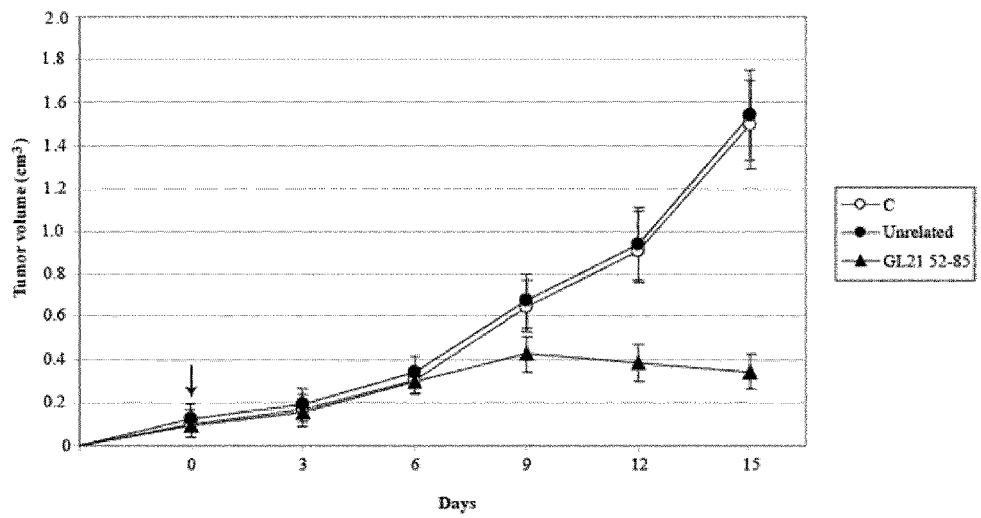
FIG. 8. GL21 52-85 aptamer inhibits tumor growth. GL21 52-85 aptamer or the unrelated aptamer were administered intra-tumorally in a mouse xenograft model bearing Axl-positive breast MDA-MB-231 (A) or NSCLC A549 (B) cancer cells. In A, "C" is control, untreated mice group.
Figure 8:
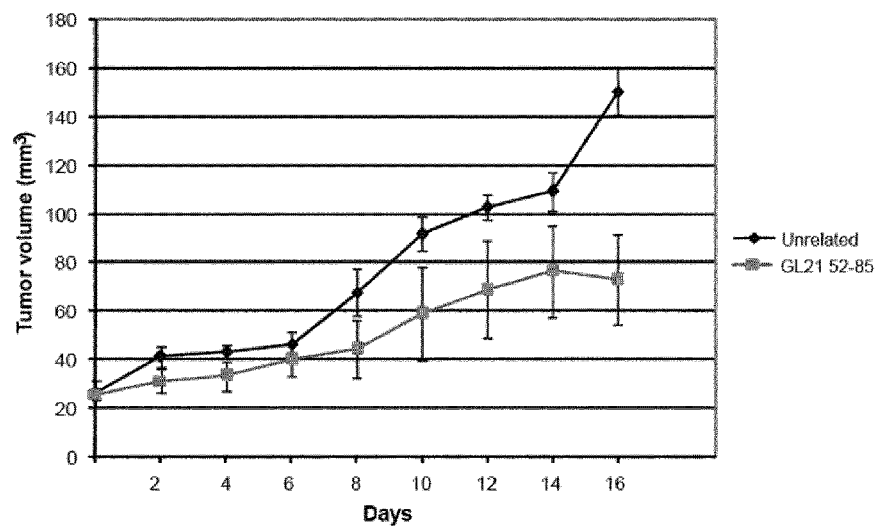

To this aim, nude mice were inoculated with the human breast tumor line MDA-MB-231 (FIG. 8 A) or A549 (FIG. 8 B) cells expressing high levels of Axl and tumors were allowed to grow until they reached about 1 cm in diameter in the longest dimension. Tumors were then injected (Day 0) with 100 µl (200 pmoles-final concentration) of GL21 52-85 aptamer or the unrelated RNA used as negative control. The injections were administered three times a week for the following two weeks. Tumors were measured every 3 days. As shown in FIG. 8, a pronounced reduction in tumor volume is observed in the presence of the GL21 52-85 aptamer. Indeed, from day 9 to day 15 the GL21 52-85-treated MDA-MB-231 tumors stopped to grow and had a reduction in volume. Accordingly, in A549-mouse xenografts a pronounced reduction in tumor volume was observed in the presence of GL21 52-85-treatment, leading at day 16 to 55% inhibition with respect to the negative control. Suppression of tumor volume was specific to the GL21 52-85-treated group and was not observed with the unrelated RNA.

DISCUSSION

The receptor tyrosine kinase Axl is expressed in various types of cancer and is involved in multiple processes of tumorigenesis, including promoting tumor cell growth, migration, invasion, metastasis as well as angiogenesis, resulting as an attractive target for therapeutic strategies.

In the present invention, the authors have identified a synthetic nuclease resistant RNA aptamer named GL21 52-85, directed to the extracellular domain of the human Axl receptor.

The authors have demonstrated that the GL21 52-85 aptamer recognizes specifically the Axl receptor expressed on the surface of cancer cells (non small cell lung cancer, breast, glioma) as well as the purified soluble extracellular domain of the receptor. On the other hand, it does not bind to cell lines that do not express Axl.

The treatment of Axl-positive cancer cells with the aptamer strongly inhibits basal and ligand-mediated Axl activation, leading to inactivation of Axl downstream signaling with a reduction of ERK phosphorylation. Further, GL21 52-85 inhibits proliferation of cancer cells in vitro.

Previous studies have established the role of Axl in promoting tumor cell growth (Shieh et al., 2005; Sainaghi et al., 2005; Zhang et al., 2008; Koorstra et al., 2009; Hutterer et al., 2008; Li et al., 2009; Ye et al., 2010; Holland et al., 2010). The authors have tested the anti-tumoral efficacy of GL21 52-85 aptamer in xenograft model of human breast MDA-MB-231 cancer cells. Remarkably, as a consequence of the Axl inhibition, GL21 52-85 aptamer resulted able to strongly inhibit tumor growth.

The data of the present invention are persuasive evidence for the clinical development of GL21 52-85 aptamer as an innovative inhibitor of Axl for both therapeutic and diagnosis scopes.

In conclusion, the identification of a neutralizing RNA-aptamer specifically targeting the Axl receptor opens the ways to the development of innovative cancer diagnostic and therapeutic strategies.

BIBLIOGRAPHIC REFERENCES

Cerchia L, de Franciscis V, Condorelli G. "Method for obtaining oligonucleotide aptamers and uses thereof", International patent application WO 2010/023327.
Cerchia L, de Franciscis V (2010) Trends Biotechnol. 28(10): 517-525.
Cerchia L, et al., (2009) PLoS One4 (11): e7971.
Cerchia L, et al., (2002) FEBS Letters 538: 12-16.
Chung B I, et al., (2003) DNA Cell Biol 22: 533-540.
Ellington A D, Szostak J W (1990) Nature 46: 818-822.
Graham D K, Sarher S L. "Axl tyrosine kinase inhibitors and methods of making and using the same", International patent application WO2008098139.
Hafizi S, Dahlbäck B (2006) Cytokine Growth Factor Rev. 17(4):295-304.
Holland S J, Pan A, Franci C, Hu Y et al. (2010) Cancer Res 70(4): 1544-1554.
Hutterer M, Knyazev P, Abate A, Reschke M et al. (2008) Clin Cancer Res 14: 130-138.
Janssen J W, et al. (1991) Oncogene 6: 2113-2120.
Koorstra J B, et al. (2009) Cancer Biol Ther 8: 618-626.
Li Y, Ye X, Tan C, Hongo J A et al. (2009) Oncogene 28: 3442-3455.
Linger R M, Keating A K, Earp H S, Graham D K (2008) Adv Cancer Res 100:35-83.
Meric F, Lee W P, Sahin A, Zhang H et al. (2002) Clin Cancer Res 8: 361-367.
O'Bryan J P, et al. (1991) Mol Cell Biol 11: 5016-5031.
Sainaghi P P, et al. (2005) J Cell Physiol 204: 36-44.
Shieh Y S, et al. (2005) Neoplasia 7: 1058-1064.
Tuek C, Gold L (1990) Science 249: 505-510.
Vajkoczy P, et al. (2006) Proc. Natl. Acad. Sci. USA 103: 5799-804.
Wu C W, Li A F, Chi C W, Lai C H et al. (2002) Anticancer Res 22: 1071-1078
Ye X, et al. (2010) Oncogene July 5.
Zhang Y X et al. (2008) Cancer Res 68: 1905-1915.

The invention claimed is:

1. A method of treating an Axl receptor tyrosine kinase induced disorder, comprising administering a nucleotide aptamer having the sequence:
5'-AUGAUCAAUCGCCUCAAUUCGACAGGAG-GCUCAC-3' (SEQ ID NO: 1) to a patient in need thereof;
wherein the Axl receptor tyrosine kinase induced disorder is selected from the group consisting of a cancer and a primary tumour metastasis.

2. The method according to claim 1, wherein the nucleotide aptamer is nuclease-resistant.

3. The method according to claim 1, wherein all of the pyrimidine residues of the nucleotide aptamer are modified to 2'-fluoropyrimidines.

4. The method according to claim 1 wherein the cancer or primary tumour metastasis is selected from the group consisting of: breast cancer, colon cancer, prostate cancer, lung cancer, gastric cancer, ovarian cancer, endometrial cancer, renal cancer, hepatocellular cancer, thyroid cancer, uterine cancer, esophageal carcinoma, squamous cell carcinoma, leukemia, osteosarcoma, melanoma, glioblastoma and neuroblastoma.

5. The method of claim 4 wherein the Axl receptor tyrosine kinase induced disorder is a primary tumour metastasis.

6. The method of claim 4 wherein the Axl receptor tyrosine kinase induced disorder is a cancer.

* * * * *